(12) United States Patent
Orten

(10) Patent No.: US 6,324,289 B2
(45) Date of Patent: *Nov. 27, 2001

(54) PICK-UP HEAD FOR AN ELECTRONIC STETHOSCOPE

(75) Inventor: Birger Orten, Alesund (NO)

(73) Assignee: Meditron A/S, Asker (NO)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/066,395
(22) PCT Filed: Nov. 14, 1996
(86) PCT No.: PCT/NO96/00268
§ 371 Date: May 8, 1998
§ 102(e) Date: May 8, 1998
(87) PCT Pub. No.: WO97/17897
PCT Pub. Date: May 22, 1997

(30) Foreign Application Priority Data

Nov. 16, 1995 (NO) .................................................. 954636

(51) Int. Cl.⁷ ........................................................ A61B 7/04
(52) U.S. Cl. ........................................... 381/67; 600/528
(58) Field of Search ............................ 381/67; 181/131; 600/528

(56) References Cited

U.S. PATENT DOCUMENTS

| | | | |
|---|---|---|---|
| 3,790,712 | * 2/1974 | Andries | 381/67 |
| 5,812,678 | * 9/1998 | Scalise et al. | 381/67 |
| 5,931,792 | * 8/1999 | Packard et al. | 600/528 |
| 6,026,170 | * 2/2000 | Dieken et al. | 381/67 |

FOREIGN PATENT DOCUMENTS

| | | |
|---|---|---|
| 932268 | 8/1955 | (DE) . |
| 2703781 | 8/1978 | (DE) . |
| 501819 | 3/1939 | (GB) . |

* cited by examiner

Primary Examiner—Forester W. Isen
Assistant Examiner—Brian Pendleton
(74) Attorney, Agent, or Firm—Laadas & Parry

(57) ABSTRACT

The pick-up head (1) with an acousto-electrical transducer (4) for converting sound vibrations to electrical signals, comprises as characterizing features a sound influencing bell (2) arranged around a slender peg (3) bonded directly to the transducer (4), and the sound influencing bell (2) delimits a listening area on a body surface and influences to a predetermined degree and in a predetermined manner, by means of internal reflection and/or absorption, the direct sound picked up by the slender center peg (3). The bell (2) is acoustically decoupled from the center peg (3).

8 Claims, 4 Drawing Sheets

PICK-UP HEAD FOR AN ELECTRONIC STETHOSCOPE

Figure 1:
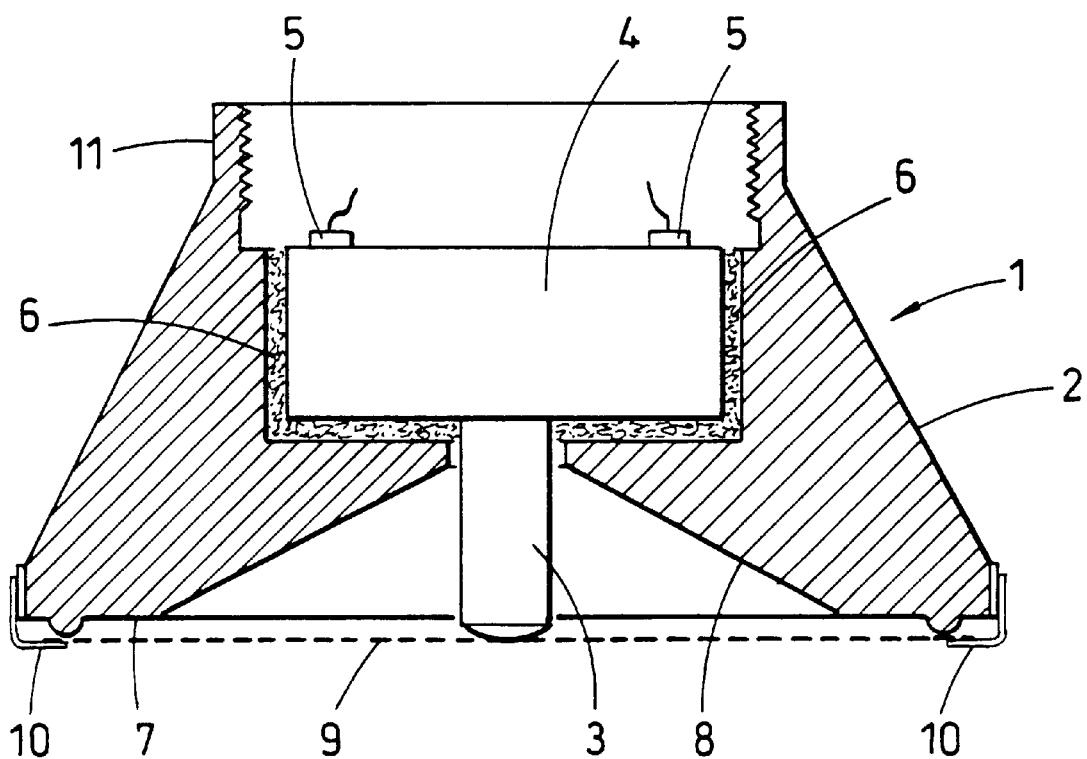

The present invention relates to electronic stethoscopes, and more particularly a pick-up head for an electronic stethoscope.

Stethoscopes are utilized within the industry, specially when listening for certain sounds which may indicate defects in machines, but are primarily used in the field of medicine for listening to sounds in connection with special body functions. Of particular interest are sounds in connection with important organs like lungs, heart and veins.

A doctor will often listen for particular sounds among a plurality of sounds received simultaneously. The various sounds often correspond to special frequency bands, and in this connection it is referred to the appended FIG. 4 which shows sound frequency bands attached to special types of heart diseases. For example, a doctor who is interested in a symptom of the type mitral stenosis, achieves a substantial improvement if frequencies above about 80 Hz can be removed, since sounds having frequencies above 80 Hz in general can be attached to other phenomena than this type of heart constriction.

Various techniques can be utilized for processing the sound frequency ranges desired to be transmitted from the body to the doctor's ear or to a sound recording apparatus. E.g. in the present applicant's own Norwegian patent application no. 95.0495 there is disclosed an electronic apparatus having an adjustable bandpass filter for removing undesired frequencies, i.e. removing "noise" so as to transmit only sounds of interest for the particular diagnosis in question. However, it is also possible to attack the problem of frequency-shaping and adaptation of sound frequencies already in the microphone itself, or in the pick-up part of the stethoscope. Ordinary stethoscopes without electronic amplification have already been provided with special pick-up head designs for achieving attenuation/amplification of different frequency bands, e.g. GB 2,051,584A and U.S. Pat. No. 4,903,794, both of which disclose stethoscope pick-up heads having special chambers designed to provide resonance at certain frequencies. In both these publications, the sound pick-up head has a forward diaphragm shaped with a centrally situated, forward protruding tip for direct engagement against a body surface.

Stethoscopes of the electronic type, i.e. having acousto-electrical transducers, and of a type somewhat related to the present invention as to design, are previously known from DE 2,703,781, DE 2,453,926 and DE 932,268. DE 2,703,781 discloses a body sound pick-up device having a piezo-electric member. For transmission of vibrations to this member, there is arranged a central and protruding pin in a cylindrical opening. The purpose is to avoid receiving of sound via the air. No measure for shaping the frequency of picked up sound, can be found.

DE 2,453,926 shows an electronic stethoscope wherein the sound pick-up member has a forward diaphragm having a centrally situated, forward protruding "scull cap". However, sound vibrations are transmitted further through an air space inside the diaphragm to an inside mounted microphone member. Special features for emphasizing/attenuating certain frequency bands are not mentioned.

DE 932,268 discloses a microphone for picking up body sounds, where a center peg transmits vibrations from a body surface to an acousto-electrical converter via a quasi-rigid mechanical connection. The center peg is surrounded by a forward projecting circular edge which has as its purpose to provide an approximately constant engagement force for the center peg against the skin. No means can be found for influencing the transmitted sound regarding removal of undesired sounds and undesired frequencies.

The object of the present invention is to provide a sound pick-up head for use as a part of an electronic stethoscope, where particularly interesting frequency ranges for special diagnosis purposes are emphasized by means of the pick-up head construction itself, at the sacrifice of other frequency ranges.

In accordance with the invention, the object is achieved by providing a sound pick-up head of the type which is defined precisely in the appended patent claims. Thus, the central feature of the invention is that at least one slender peg for conveying vibrations is arranged centrally inside a sound-affecting bell which delimits with its edge a reflection and/or absorption space surrounding the slender peg, in such a manner that certain frequencies are reflected in toward the peg, and other frequencies are prevented from such reflection, whereby the peg conveys frequency-shaped sound. The bell itself is acoustically decoupled from the slender peg, which in itself picks up sound only from a very small area of the body surface, while sound supplied to the peg secondarily after reflection inside the bell, in principle originates from the larger, bounded body surface area under the bell.

Figure 2:
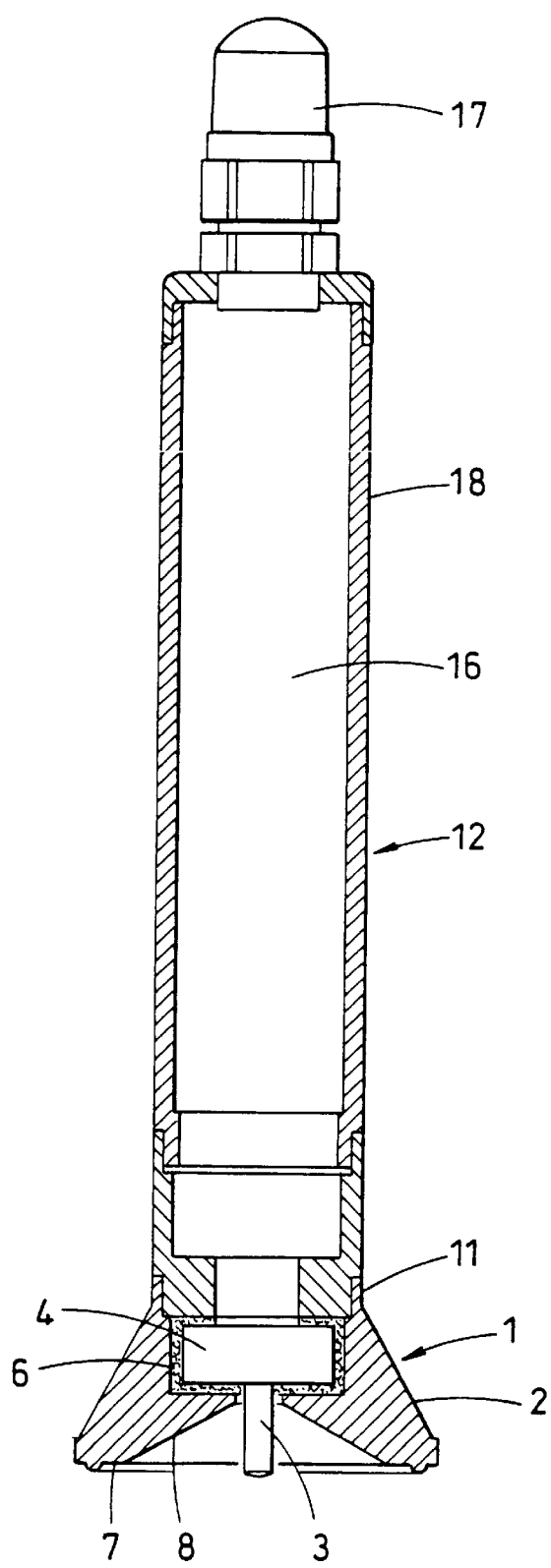
Figure 3:
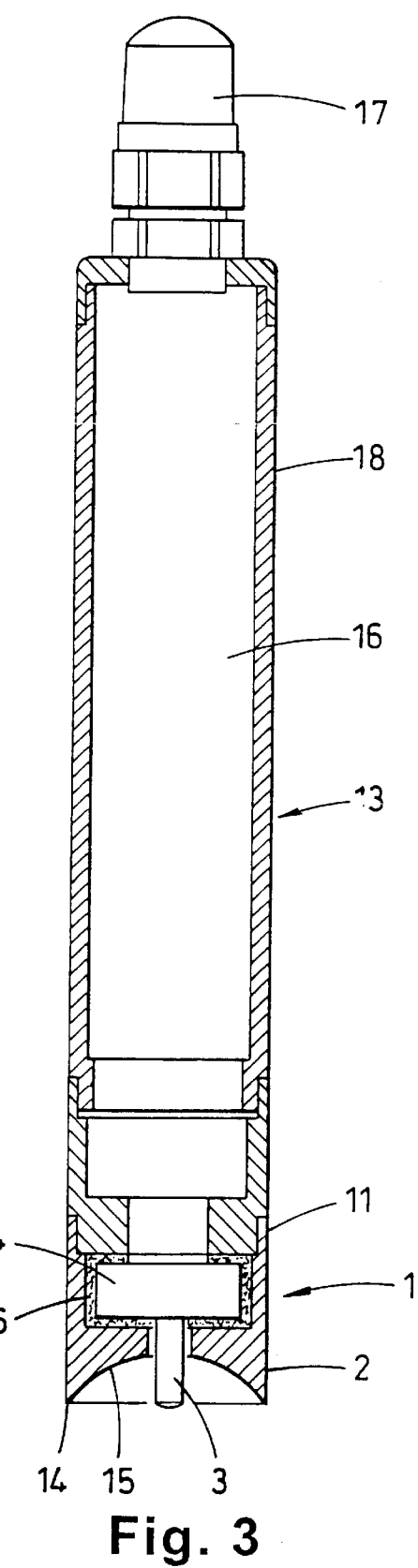
Figure 4:
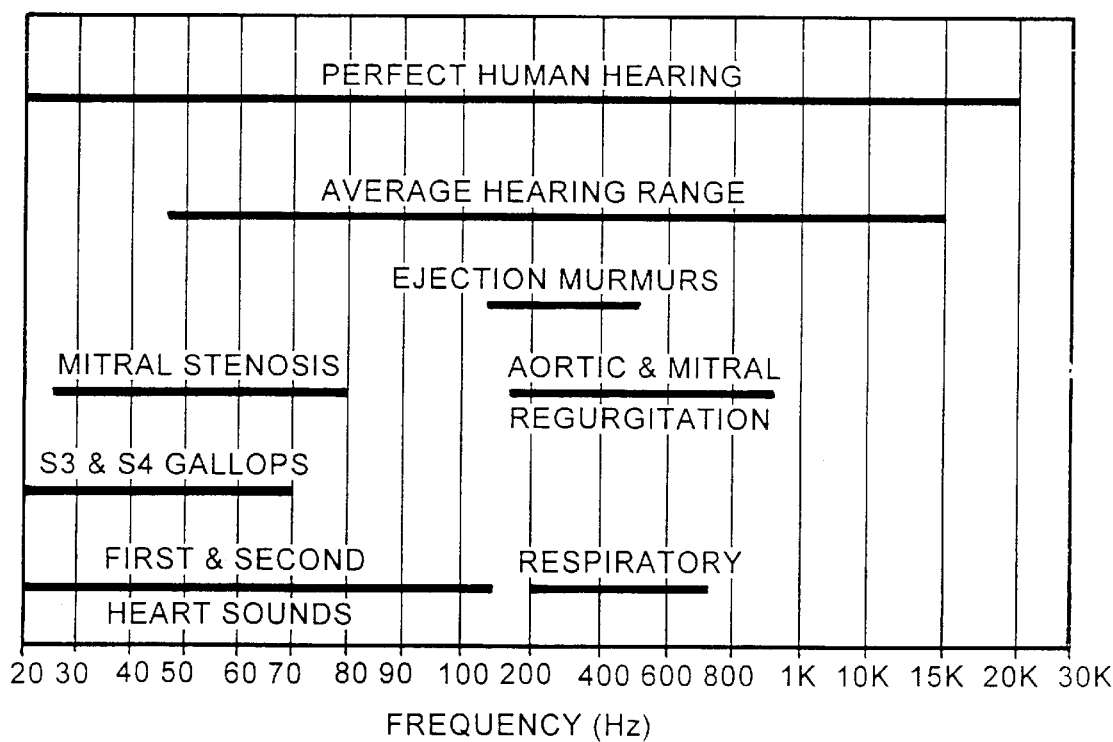
Figure 5:
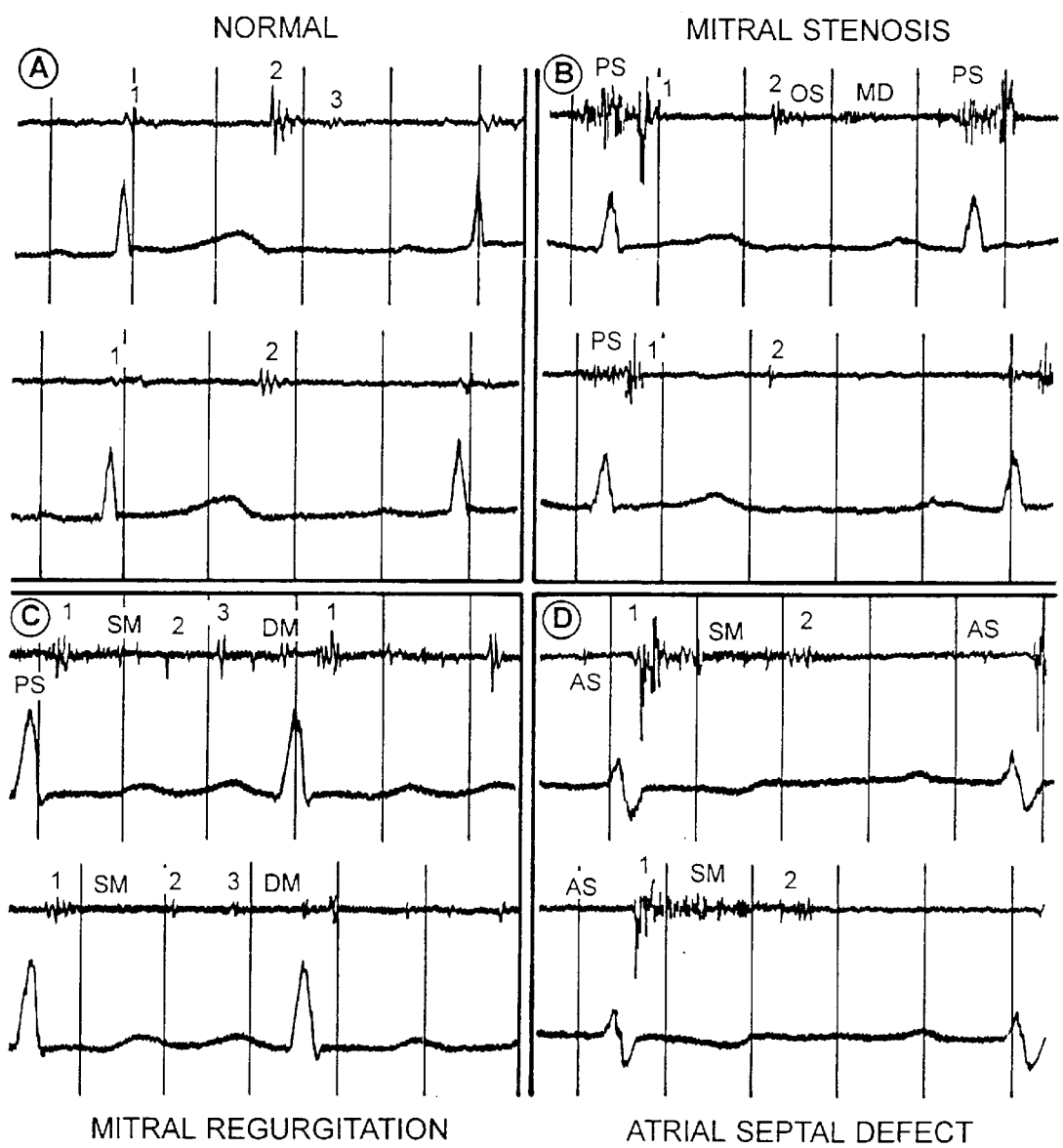

In the following the invention will be explained in closer detail by means of embodiment examples, and it is at the same time referred to the appended drawings, in which FIG. 1 shows an embodiment of a pick-up head in accordance with the invention, FIG. 2 shows a pick-up head of the type shown in FIG. 1, mounted together with an electronics part to constitute a complete electronic stethoscope, FIG. 3 shows a complete stethoscope of the same general type as in FIG. 2, however with a different design of the pick-up head reflector bell, FIG. 4 is a frequency diagram indicating effective sound frequency ranges for certain heart diseases, and FIG. 5 shows conventionally recorded phonocardiographic curves.

In FIG. 1 is shown a basic embodiment of the pick-up head of the invention. The pick-up head itself is shown with reference numeral 1, and it comprises as its most important elements a sound influencing bell 2, a center peg 3 and an acousto-electrical transducer means 4. The peg 3 is bonded directly to the transducer 4, which is adapted to provide connection to electronic amplifying and processing circuitry which is not shown in the figure, via electrical contact points 5. The sound influencing bell 2 is acoustically decoupled from the transducer 4 by means of a vibration absorbing lining 6.

The figure should be perceived as a section through the pick-up head 1, and an obvious pick-up head shape is that it is circular symmetrical about a center axis which coincides with the longitudinal axis of the center peg. However, the shape may also be oval, or possibly such that the bell 2 has a square circumference, or for that matter a triangular or multi-sided circumference.

The sound influencing bell 2 of the pick-up head delimits the listening area on a body surface when the edge area 7 engages the surface. Sound emanating from the delimited listening area on the body surface can then be reflected against the inside wall 8 in the sound influencing bell 2 and toward the center peg 3 to provide extra sound in addition to the sound picked up directly by the peg from a very small central area engaged by the peg. Important parameters in this connection are the shape of the inside wall, i.e. the possible curvature or flatness thereof, the slant angle B between the inside wall 8 and the plane of the edge area 7, and further the material of the inside wall 8 and the sound frequencies present. A doubly-curved inside wall 8, e.g. with a parabolic curvature in the cross section, will provide a focusing effect in toward a certain position on the center peg 3, while a conical inside wall 8 as shown in FIG. 1 (that is when the figure shows a cross section through a circular symmetrical pick-up head), will spread reflected sound more toward the full extent of the peg. Thus, the different shapes of the inside wall 8 will be of importance regarding arrival times to the transducer 4 for different parts of the total sound signal from the delimited area of the body surface, and it is possible to "tailor" the shape of the inside wall 8 to provide the best possible response for the pick-up head in relation to particularly interesting body sounds. Of course, also an embodiment (not shown) of the invention will be to provide a pick-up head inside wall 8 with a changeable shape, preferably in such manner that one single, finger-operated button on the outside of the pick-up head gives a change of shape by direct mechanical transmission to a tightening member which forces the inside wall 8 to change its curvature, and thereby also provides a different total response for the pick-up head.

It is also possible to give an area or certain areas of the inside wall 8 different sound-reflecting or sound-absorbing properties, also depending on frequency, in order to influence the pick-up head response in a desired direction regarding a favourable transmission of special sounds. In one variant of the invention, the sound influencing bell is equipped with a purely absorbing inside wall. This will make it possible to remove echoes and acoustics from the bell, and only the center peg will then pass on sound vibrations to the transducer 4.

Among further variable parameters of the pick-up head 1, the center peg 3 itself must be mentioned, which center peg as a starting point is a stiff and elongate rod of a hard material, e.g. steel. However, the pick-up head may be equipped with a number of such pegs, centrally arranged inside the sound influencing bell 2. The pegs may then be connected to one single acousto-electrical transducer means 4, or separate transducers may be arranged for each respective peg, in order to obtain double, triple, etc. sound pickup. In such "multi-peg" cases, the peg angles may deviate from a precise axial direction (relative to the shown one-peg case of FIG. 1), and the direction to and the depth of sound sources inside the body surface can then possibly be calculated by means of attached electronic circuitry and computer equipment.

While underlining that the gist of the present invention is the special combination of direct sound from a small central area, provided by means of a (or a number of) slender center peg(s), and reflected sound from the larger, delimited body surface area via the inside of the sound influencing bell and to the center peg, with a "purpose-adapted" size and shape of the bell inside wall 8, one particular, further embodiment should be noted: It is possible to change the properties of the pick-up head beyond what has been mentioned above, by tautening a diaphragm 9, shown in FIG. 1 as a broken line, over the entire opening of the sound influencing bell, i.e. outside the forward protruding center peg 3. A fastening means 10 for the diaphragm 9 must then be provided around the outer edge of the bell. The effect of such a diaphragm is that the center peg, which then engages the diaphragm, will catch sounds from a larger area, however this solution will also give more contact noise from the body surface area of interest, and will normally not be a preferred solution.

In FIG. 1, the pick-up head is equipped on top with a socket 11. In the embodiments appearing from FIGS. 2 and 3, it appears that the socket 11 is used to provide complete stethoscopes 12, 13 with a shape approximately like a flashlight, where an elongate main body 18 contains complete amplifying and processing circuitry in an electronics part 16, connected to the transducer means 4 via the contact points 5 (see. FIG. 1). Reference numeral 17 indicates schematically an antenna of the radio type, optionally for transmitting modulated light, or for transmitting ultrasound, and in any case for transmitting information-carrying radiation which is received by a stationary (not shown) receiver apparatus. Of course a wire connection is also possible, but then the hand-held unit 12, 13 may actually be reduced to merely unit 1, with wires from the contact points 5 to a more complete, stationary signal processing unit, the pick-up head 1 itself then constituting the hand-held unit.

In FIG. 2 the pick-up head 1 is of substantially the same type as shown in FIG. 1, while in FIG. 3 is shown a doubly-curved inside wall 15 in the sound influencing bell 2. The edge area of the bell is in this case shaped more sharply as an edge 14.

FIG. 4 shows a diagram regarding the location within the audible range of special sounds attached to particular heart disease symptoms. It is to be noted, in comparison with the audible range (20 Hz–20 kHz) and the range of typical respiratory sounds (200–700 Hz), that respectively mitral stenosis has typical frequencies in the range 25–80 Hz, the first and second heart sounds occur with frequencies in the range 20–140 Hz, the atrial septal defect in the range 20–70 Hz, aortic and mitral regurgitation provides sounds having frequencies in the range 170–900 Hz, and ejection murmurs are typically situated at 130–500 Hz. The pick-up head in accordance with the invention can be used just to accentuate such special frequency ranges, or to suppress the transmission of outside frequencies, if this is the more desirable view.

It is to be noted that the pick-up head in accordance with the invention turns out to provide good results also when listening on the outside of clothes.

In use, the sound influencing bell forms a closed space around the center peg, and hence has the effect that sounds coming from the outside area, will not be picked up by the peg. Thus, the bell also functions as a shield against other signals than "usable signals". Only body sounds picked up inside the bell shall be valid, and undesired signals shall be removed.

It has previously been stated that different shapes of a reflecting inside wall in the sound influencing bell will provide reflections that can be directed substantially toward one position on the center peg, or in a more spread-out fashion toward various positions. Thus, the shape of the inside wall can be adapted to compensate for different arrival times for different sounds, whereby certain arrivals can be suppressed and other arrivals can be emphasized. Arrival time as a consequence of the geometrical shape and the choice of material of the sound influencing bell, is an important parameter. The fact that the bell provides reflections scattered toward different positions at different times, will give a phase shift in time/sound. See e.g. the curve portions shown in FIG. 5, recorded using traditional phonocardiography. Such curves may to a certain degree be rendered sharper, better defined and simpler to interpret by means of the emphasis and accentuation which can be achieved by the pick-up head in accordance with the invention.

What is claimed is:
1. A pick-up head for an electronic stethoscope, comprising at least one acousto-electrical transducer for providing at least one electrical signal representing acoustical vibrations, and at least one mechanical member coupled to said transducer for conveying said acoustical vibrations from a body surface to said transducer, wherein a sound influencing bell, which is acoustically decoupled from said at least one mechanical member, is arranged therearound for providing with an edge a delimited listening area on said body surface and for providing with its inside walls a sound-influencing cavity surface surrounding said at least one mechanical member and being adapted to reflect sound toward said at least one mechanical member, being adapted to reflect sound toward said at least one mechanical member, cavity wall angles, wall radii of curvature and wall surface material being decisive parameters regarding reflecting certain sound frequencies, and said at least one mechanical member is constituted by a straight, slender peg which is operative to pick-up at its front acoustical vibrations from said body surface through a peg front area that is a substantially smaller area than said delimited listening area, and laterally reflected, acoustical vibrations reflected from said cavity walls.

2. The pick-up head of claim 1, wherein a number of slender pegs for picking up acoustical vibrations, are coupled to one single acousto-electrical transducer.

3. The pick-up head of claim 1, wherein a number of slender pegs for picking up acoustical vibrations, are coupled to respective ones of a corresponding number of acousto-electrical transducers for proving a corresponding number of separate electrical signals.

4. The pick-up head of claim 1, wherein the edge of said sound influencing bell is substantially flat and has a selected geometrical shape.

5. The pick-up head of claim 1, wherein at least an area of the wall(s) is adapted to absorb sound within a predetermined frequency range.

6. The pick-up head of claim 1, wherein a diaphragm is fastened along the edge of said sound influencing bell to engage the body surface between said at least one peg and said body surface.

7. The pick-up head of claim 1, wherein electronic circuitry for processing the electrical signals is included in a unit which is integrated with or mounted on said pick-up head.

8. The pick-up head of claim 7, wherein said unit includes a transmitter for communication with a computer.

* * * * *